United States Patent [19]
Goeddel et al.

[11] Patent Number: 5,851,812
[45] Date of Patent: Dec. 22, 1998

[54] IKK-β PROTEINS, NUCLEIC ACIDS AND METHODS

[75] Inventors: David V. Goeddel, Hillsborough; John Woronicz, South San Francisco, both of Calif.

[73] Assignee: Tularik Inc., South San Francisco, Calif.

[21] Appl. No.: 890,853

[22] Filed: Jul. 10, 1997

Related U.S. Application Data

[63] Continuation of Ser. No. 887,114, Jul. 1, 1997, abandoned.

[51] Int. Cl.$^6$ ............................... C12N 1/21; C12N 5/10; C12N 9/12; C12N 15/54

[52] U.S. Cl. ..................... 435/194; 435/252.3; 435/325; 536/23.2

[58] Field of Search ........................ 536/23.2; 435/325, 435/252.3, 194

[56] References Cited

PUBLICATIONS

Koyama et al., Genomics 26:245–253, 1995.
Jung et al., Cancer Res. 57:24–27, 1997.
Kumar et al., Proc. Natl. Acad. Sci. USA 91:6288–6292, 1994.
Schouten et al., EMBO J. 16:3133–3144, 1997.
McElhinny et al., Mol. Cell. Biol. 16:899–906, 1996.

*Primary Examiner*—Eric Grimes
*Attorney, Agent, or Firm*—Richard Aron Osman

[57] ABSTRACT

The invention provides methods and compositions relating to an IκB kinase, IKK-β, and related nucleic acids. The polypeptides may be produced recombinantly from transformed host cells from the disclosed IKK-β encoding nucleic acids or purified from human cells. The invention provides isolated IKK-β hybridization probes and primers capable of specifically hybridizing with the disclosed IKK-β genes, IKK-β-specific binding agents such as specific antibodies, and methods of making and using the subject compositions in diagnosis, therapy and in the biopharmaceutical industry.

12 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2268 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
ATGAGCTGGT  CACCTTCCCT  GACAACGCAG  ACATGTGGGG  CCTGGGAAAT  GAAAGAGCGC      60

CTTGGGACAG  GGGGATTTGG  AAATGTCATC  CGATGGCACA  ATCAGGAAAC  AGGTGAGCAG     120

ATTGCCATCA  AGCAGTGCCG  GCAGGAGCTC  AGCCCCGGA   ACCGAGAGCG  GTGGTGCCTG     180

GAGATCCAGA  TCATGAGAAG  GCTGACCCAC  CCCAATGTGG  TGGCTGCCCG  AGATGTCCCT     240

GAGGGGATGC  AGAACTTGGC  GCCCAATGAC  CTGCCCCTGC  TGGCCATGGA  GTACTGCCAA     300

GGAGGAGATC  TCCGGAAGTA  CCTGAACCAG  TTTGAGAACT  GCTGTGGTCT  GCGGGAAGGT     360

GCCATCCTCA  CCTTGCTGAG  TGACATTGCC  TCTGCGCTTA  GATACCTTCA  TGAAAACAGA     420

ATCATCCATC  GGGATCTAAA  GCCAGAAAAC  ATCGTCCTGC  AGCAAGGAGA  ACAGAGGTTA     480

ATACACAAAA  TTATTGACCT  AGGATATGCC  AAGGAGCTGG  ATCAGGGCAG  TCTTTGCACA     540

TCATTCGTGG  GGACCCTGCA  GTACCTGGCC  CCAGAGCTAC  TGGAGCAGCA  GAAGTACACA     600

GTGACCGTCG  ACTACTGGAG  CTTCGGCACC  CTGGCCTTTG  AGTGCATCAC  GGGCTTCCGG     660

CCCTTCCTCC  CCAACTGGCA  GCCCGTGCAG  TGGCATTCAA  AAGTGCGGCA  GAAGAGTGAG     720

GTGGACATTG  TTGTTAGCGA  AGACTTGAAT  GGAACGGTGA  AGTTTCAAG   CTCTTTACCC     780

TACCCCAATA  ATCTTAACAG  TGTCCTGGCT  GAGCGACTGG  AGAAGTGGCT  GCAACTGATG     840

CTGATGTGGC  ACCCCCGACA  GAGGGGCACG  GATCCCACGT  ATGGGCCCAA  TGGCTGCTTC     900

AAGGCCCTGG  ATGACATCTT  AAACTTAAAG  CTGGTTCATA  TCTTGAACAT  GGTCACGGGC     960

ACCATCCACA  CCTACCCTGT  GACAGAGGAT  GAGAGTCTGC  AGAGCTTGAA  GGCCAGAATC    1020

CAACAGGACA  CGGGCATCCC  AGAGGAGGAC  CAGGAGCTGC  TGCAGGAAGC  GGGCCTGGCG    1080

TTGATCCCCG  ATAAGCCTGC  CACTCAGTGT  ATTTCAGACG  GCAAGTTAAA  TGAGGGCCAC    1140

ACATTGGACA  TGGATCTTGT  TTTTCTCTTT  GACAACAGTA  AAATCACCTA  TGAGACTCAG    1200

ATCTCCCCAC  GGCCCCAACC  TGAAAGTGTC  AGCTGTATCC  TTCAAGAGCC  CAAGAGGAAT    1260

CTCGCCTTCT  TCCAGCTGAG  GAAGGTGTGG  GGCCAGGTCT  GGCACAGCAT  CCAGACCCTG    1320

AAGGAAGATT  GCAACCGGCT  GCAGCAGGGA  CAGCGAGCCG  CCATGATGAA  TCTCCTCCGA    1380

AACAACAGCT  GCCTCTCCAA  AATGAAGAAT  TCCATGGCTT  CCATGTCTCA  GCAGCTCAAG    1440

GCCAAGTTGG  ATTTCTTCAA  AACCAGCATC  CAGATTGACC  TGGAGAAGTA  CAGCGAGCAA    1500
```

```
ACCGAGTTTG  GGATCACATC  AGATAAACTG  CTGCTGGCCT  GGAGGGAAAT  GGAGCAGGCT      1560

GTGGAGCTCT  GTGGGCGGGA  GAACGAAGTG  AAACTCCTGG  TAGAACGGAT  GATGGCTCTG      1620

CAGACCGACA  TTGTGGACTT  ACAGAGGAGC  CCCATGGGCC  GGAAGCAGGG  GGGAACGCTG      1680

GACGACCTAG  AGGAGCAAGC  AAGGGAGCTG  TACAGGAGAC  TAAGGGAAAA  ACCTCGAGAC      1740

CAGCGAACTG  AGGGTGACAG  TCAGGAAATG  GTACGGCTGC  TGCTTCAGGC  AATTCAGAGC      1800

TTCGAGAAGA  AAGTGCGAGT  GATCTATACG  CAGCTCAGTA  AAACTGTGGT  TTGCAAGCAG      1860

AAGGCGCTGG  AACTGTTGCC  CAAGGTGGAA  GAGGTGGTGA  GCTTAATGAA  TGAGGATGAG      1920

AAGACTGTTG  TCCGGCTGCA  GGAGAAGCGG  CAGAAGGAGC  TCTGGAATCT  CCTGAAGATT      1980

GCTTGTAGCA  AGGTCCGTGG  TCCTGTCAGT  GGAAGCCCGG  ATAGCATGAA  TGCCTCTCGA      2040

CTTAGCCAGC  CTGGGCAGCT  GATGTCTCAG  CCCTCCACGG  CCTCCAACAG  CTTACCTGAG      2100

CCAGCCAAGA  AGAGTGAAGA  ACTGGTGGCT  GAAGCACATA  ACCTCTGCAC  CCTGCTAGAA      2160

AATGCCATAC  AGGACACTGT  GAGGGAACAA  GACCAGAGTT  TCACGGCCCT  AGACTGGAGC      2220

TGGTTACAGA  CGGAAGAAGA  AGAGCACAGC  TGCCTGGAGC  AGGCCTCA                    2268
```

( 2 ) INFORMATION FOR SEQ ID NO:2:

( i ) SEQUENCE CHARACTERISTICS:
        ( A ) LENGTH: 756 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met Ser Trp Ser Pro Ser Leu Thr Thr Gln Thr Cys Gly Ala Trp Glu
 1               5                  10                 15

Met Lys Glu Arg Leu Gly Thr Gly Gly Phe Gly Asn Val Ile Arg Trp
            20                  25                  30

His Asn Gln Glu Thr Gly Glu Gln Ile Ala Ile Lys Gln Cys Arg Gln
        35                  40                  45

Glu Leu Ser Pro Arg Asn Arg Glu Arg Trp Cys Leu Glu Ile Gln Ile
    50                  55                  60

Met Arg Arg Leu Thr His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Lys Tyr Leu Asn Gln Phe Glu
            100                 105                 110

Asn Cys Cys Gly Leu Arg Glu Gly Ala Ile Leu Thr Leu Leu Ser Asp
        115                 120                 125

Ile Ala Ser Ala Leu Arg Tyr Leu His Glu Asn Arg Ile Ile His Arg
    130                 135                 140

Asp Leu Lys Pro Glu Asn Ile Val Leu Gln Gln Gly Glu Gln Arg Leu
145                 150                 155                 160

Ile His Lys Ile Ile Asp Leu Gly Tyr Ala Lys Glu Leu Asp Gln Gly
                165                 170                 175

Ser Leu Cys Thr Ser Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
        195                 200                 205

Gly Thr Leu Ala Phe Glu Cys Ile Thr Gly Phe Arg Pro Phe Leu Pro
    210                 215                 220
```

-continued

```
Asn  Trp  Gln  Pro  Val  Gln  Trp  His  Ser  Lys  Val  Arg  Gln  Lys  Ser  Glu
225                 230                      235                           240

Val  Asp  Ile  Val  Val  Ser  Glu  Asp  Leu  Asn  Gly  Thr  Val  Lys  Phe  Ser
                    245                 250                      255

Ser  Ser  Leu  Pro  Tyr  Pro  Asn  Asn  Leu  Asn  Ser  Val  Leu  Ala  Glu  Arg
               260                 265                      270

Leu  Glu  Lys  Trp  Leu  Gln  Leu  Met  Leu  Met  Trp  His  Pro  Arg  Gln  Arg
               275                 280                      285

Gly  Thr  Asp  Pro  Thr  Tyr  Gly  Pro  Asn  Gly  Cys  Phe  Lys  Ala  Leu  Asp
               290                 295                      300

Asp  Ile  Leu  Asn  Leu  Lys  Leu  Val  His  Ile  Leu  Asn  Met  Val  Thr  Gly
305                 310                      315                           320

Thr  Ile  His  Thr  Tyr  Pro  Val  Thr  Glu  Asp  Glu  Ser  Leu  Gln  Ser  Leu
                    325                 330                      335

Lys  Ala  Arg  Ile  Gln  Gln  Asp  Thr  Gly  Ile  Pro  Glu  Glu  Asp  Gln  Glu
               340                 345                      350

Leu  Leu  Gln  Glu  Ala  Gly  Leu  Ala  Leu  Ile  Pro  Asp  Lys  Pro  Ala  Thr
               355                 360                      365

Gln  Cys  Ile  Ser  Asp  Gly  Lys  Leu  Asn  Glu  Gly  His  Thr  Leu  Asp  Met
     370                 375                      380

Asp  Leu  Val  Phe  Leu  Phe  Asp  Asn  Ser  Lys  Ile  Thr  Tyr  Glu  Thr  Gln
385                 390                      395                           400

Ile  Ser  Pro  Arg  Pro  Gln  Pro  Glu  Ser  Val  Ser  Cys  Ile  Leu  Gln  Glu
               405                 410                      415

Pro  Lys  Arg  Asn  Leu  Ala  Phe  Phe  Gln  Leu  Arg  Lys  Val  Trp  Gly  Gln
               420                 425                      430

Val  Trp  His  Ser  Ile  Gln  Thr  Leu  Lys  Glu  Asp  Cys  Asn  Arg  Leu  Gln
               435                 440                      445

Gln  Gly  Gln  Arg  Ala  Ala  Met  Met  Asn  Leu  Leu  Arg  Asn  Asn  Ser  Cys
     450                 455                      460

Leu  Ser  Lys  Met  Lys  Asn  Ser  Met  Ala  Ser  Met  Ser  Gln  Gln  Leu  Lys
465                 470                      475                           480

Ala  Lys  Leu  Asp  Phe  Phe  Lys  Thr  Ser  Ile  Gln  Ile  Asp  Leu  Glu  Lys
               485                 490                      495

Tyr  Ser  Glu  Gln  Thr  Glu  Phe  Gly  Ile  Thr  Ser  Asp  Lys  Leu  Leu  Leu
               500                 505                      510

Ala  Trp  Arg  Glu  Met  Glu  Gln  Ala  Val  Glu  Leu  Cys  Gly  Arg  Glu  Asn
     515                 520                      525

Glu  Val  Lys  Leu  Leu  Val  Glu  Arg  Met  Met  Ala  Leu  Gln  Thr  Asp  Ile
     530                 535                      540

Val  Asp  Leu  Gln  Arg  Ser  Pro  Met  Gly  Arg  Lys  Gln  Gly  Gly  Thr  Leu
545                 550                      555                           560

Asp  Asp  Leu  Glu  Glu  Gln  Ala  Arg  Glu  Leu  Tyr  Arg  Arg  Leu  Arg  Glu
               565                 570                      575

Lys  Pro  Arg  Asp  Gln  Arg  Thr  Glu  Gly  Asp  Ser  Gln  Glu  Met  Val  Arg
               580                 585                      590

Leu  Leu  Leu  Gln  Ala  Ile  Gln  Ser  Phe  Glu  Lys  Lys  Val  Arg  Val  Ile
          595                 600                      605

Tyr  Thr  Gln  Leu  Ser  Lys  Thr  Val  Val  Cys  Lys  Gln  Lys  Ala  Leu  Glu
     610                 615                      620

Leu  Leu  Pro  Lys  Val  Glu  Glu  Val  Val  Ser  Leu  Met  Asn  Glu  Asp  Glu
625                 630                      635                           640

Lys  Thr  Val  Val  Arg  Leu  Gln  Glu  Lys  Arg  Gln  Lys  Glu  Leu  Trp  Asn
```

|        |        |        |        | 645     |        |        |        |        | 650    |        |        |        |        | 655     |        |
|--------|--------|--------|--------|---------|--------|--------|--------|--------|--------|--------|--------|--------|--------|---------|--------|
| Leu    | Leu    | Lys    | Ile<br>660 | Ala | Cys | Ser | Lys | Val<br>665 | Arg | Gly | Pro | Val | Ser<br>670 | Gly | Ser |
| Pro | Asp | Ser<br>675 | Met | Asn | Ala | Ser | Arg<br>680 | Leu | Ser | Gln | Pro | Gly<br>685 | Gln | Leu | Met |
| Ser | Gln<br>690 | Pro | Ser | Thr | Ala | Ser<br>695 | Asn | Ser | Leu | Pro | Glu<br>700 | Pro | Ala | Lys | Lys |
| Ser<br>705 | Glu | Glu | Leu | Val | Ala<br>710 | Glu | Ala | His | Asn | Leu<br>715 | Cys | Thr | Leu | Leu | Glu<br>720 |
| Asn | Ala | Ile | Gln | Asp<br>725 | Thr | Val | Arg | Glu | Gln<br>730 | Asp | Gln | Ser | Phe | Thr<br>735 | Ala |
| Leu | Asp | Trp | Ser<br>740 | Trp | Leu | Gln | Thr | Glu<br>745 | Glu | Glu | Glu | His | Ser<br>750 | Cys | Leu |
| Glu | Gln | Ala | Ser<br>755 |

( 2 ) INFORMATION FOR SEQ ID NO:3:

( i ) SEQUENCE CHARACTERISTICS:
       ( A ) LENGTH: 2238 base pairs
       ( B ) TYPE: nucleic acid
       ( C ) STRANDEDNESS: double
       ( D ) TOPOLOGY: linear ( i i ) MOLECULE TYPE: cDNA ( x i ) SEQUENCE DESCRIPTION: SEQ ID NO:3:

| ATGGAGCGGC | CCCCGGGGCT | GCGGCCGGGC | GCGGGCGGGC | CCTGGGAGAT | GCGGGAGCGG | 60 |
| CTGGGCACCG | GCGGCTTCGG | GAACGTCTGT | CTGTACCAGC | ATCGGGAACT | TGATCTCAAA | 120 |
| ATAGCAATTA | AGTCTTGTCG | CCTAGAGCTA | AGTACCAAAA | ACAGAGAACG | ATGGTGCCAT | 180 |
| GAAATCCAGA | TTATGAAGAA | GTTGAACCAT | GCCATGTTG | TAAAGGCCTG | TGATGTTCCT | 240 |
| GAAGAATTGA | ATATTTTGAT | TCATGATGTG | CCTCTTCTAG | CAATGGAATA | CTGTTCTGGA | 300 |
| GGAGATCTCC | GAAAGCTGCT | CAACAAACCA | GAAAATTGTT | GTGGACTTAA | AGAAAGCCAG | 360 |
| ATACTTTCTT | TACTAAGTGA | TATAGGGTCT | GGGATTCGAT | ATTTGCATGA | AAACAAAATT | 420 |
| ATACATCGAG | ATCTAAAACC | TGAAAACATA | GTTCTTCAGG | ATGTTGGTGG | AAAGATAATA | 480 |
| CATAAAATAA | TTGATCTGGG | ATATGCCAAA | GATGTTGATC | AAGGAAGTCT | GTGTACATCT | 540 |
| TTTGTGGGAA | CACTGCAGTA | TCTGGCCCCA | GAGCTCTTTG | AGAATAAGCC | TTACACAGCC | 600 |
| ACTGTTGATT | ATTGGAGCTT | TGGGACCATG | GTATTTGAAT | GTATTGCTGG | ATATAGGCCT | 660 |
| TTTTTGCATC | ATCTGCAGCC | ATTACCTGG | CATGAGAAGA | TTAAGAAGAA | GGATCCAAAG | 720 |
| TGTATATTTG | CATGTGAAGA | GATGTCAGGA | GAAGTTCGGT | TTAGTAGCCA | TTTACCTCAA | 780 |
| CCAAATAGCC | TTTGTAGTTT | AATAGTAGAA | CCCATGGAAA | ACTGGCTACA | GTTGATGTTG | 840 |
| AATTGGGACC | CTCAGCAGAG | AGGAGGACCT | GTTGACCTTA | CTTTGAAGCA | GCCAAGATGT | 900 |
| TTTGTATTAA | TGGATCACAT | TTTGAATTTG | AAGATAGTAC | ACATCCTAAA | TATGACTTCT | 960 |
| GCAAAGATAA | TTTCTTTTCT | GTTACCACCT | GATGAAAGTC | TTCATTCACT | ACAGTCTCGT | 1020 |
| ATTGAGCGTG | AAACTGGAAT | AAATACTGGT | TCTCAAGAAC | TTCTTTCAGA | GACAGGAATT | 1080 |
| TCTCTGGATC | CTCGGAAACC | AGCCTCTCAA | TGTGTTCTAG | ATGGAGTTAG | AGGCTGTGAT | 1140 |
| AGCTATATGG | TTTATTTGTT | TGATAAAAGT | AAAACTGTAT | ATGAAGGGCC | ATTTGCTTCC | 1200 |
| AGAAGTTTAT | CTGATTGTGT | AAATTATATT | GTACAGGACA | GCAAAATACA | GCTTCCAATT | 1260 |
| ATACAGCTGC | GTAAAGTGTG | GGCTGAAGCA | GTGCACTATG | TGTCTGGACT | AAAAGAAGAC | 1320 |

```
TATAGCAGGC  TCTTTCAGGG  ACAAAGGGCA  GCAATGTTAA  GTCTTCTTAG  ATATAATGCT    1380

AACTTAACAA  AAATGAAGAA  CACTTTGATC  TCAGCATCAC  AACAACTGAA  AGCTAAATTG    1440

GAGTTTTTTC  ACAAAAGCAT  TCAGCTTGAC  TTGGAGAGAT  ACAGCGAGCA  GATGACGTAT    1500

GGGATATCTT  CAGAAAAAAT  GCTAAAAGCA  TGGAAAGAAA  TGGAAGAAAA  GGCCATCCAC    1560

TATGCTGAGG  TTGGTGTCAT  TGGATACCTG  GAGGATCAGA  TTATGTCTTT  GCATGCTGAA    1620

ATCATGGAGC  TACAGAAGAG  CCCCTATGGA  AGACGTCAGG  GAGACTTGAT  GGAATCTCTG    1680

GAACAGCGTG  CCATTGATCT  ATATAAGCAG  TTAAAACACA  GACCTTCAGA  TCACTCCTAC    1740

AGTGACAGCA  CAGAGATGGT  GAAAATCATT  GTGCACACTG  TGCAGAGTCA  GGACCGTGTG    1800

CTCAAGGAGC  TGTTTGGTCA  TTTGAGCAAG  TTGTTGGGCT  GTAAGCAGAA  GATTATTGAT    1860

CTACTCCCTA  AGGTGGAAGT  GGCCCTCAGT  AATATCAAAG  AAGCTGACAA  TACTGTCATG    1920

TTCATGCAGG  GAAAAAGGCA  GAAAGAAATA  TGGCATCTCC  TTAAAATTGC  CTGTACACAG    1980

AGTTCTGCCC  GGTCCCTTGT  AGGATCCAGT  CTAGAAGGTG  CAGTAACCCC  TCAGACATCA    2040

GCATGGCTGC  CCCCGACTTC  AGCAGAACAT  GATCATTCTC  TGTCATGTGT  GGTAACTCCT    2100

CAAGATGGGG  AGACTTCAGC  ACAAATGATA  GAAGAAAATT  TGAACTGCCT  TGGCCATTTA    2160

AGCACTATTA  TTCATGAGGC  AAATGAGGAA  CAGGGCAATA  GTATGATGAA  TCTTGATTGG    2220

AGTTGGTTAA  CAGAATGA                                                     2238
```

( 2 ) INFORMATION FOR SEQ ID NO:4:

( i ) SEQUENCE CHARACTERISTICS:
    ( A ) LENGTH: 745 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

```
Met  Glu  Arg  Pro  Pro  Gly  Leu  Arg  Pro  Gly  Ala  Gly  Gly  Pro  Trp  Glu
 1                  5                       10                      15

Met  Arg  Glu  Arg  Leu  Gly  Thr  Gly  Gly  Phe  Gly  Asn  Val  Cys  Leu  Tyr
                20                       25                      30

Gln  His  Arg  Glu  Leu  Asp  Leu  Lys  Ile  Ala  Ile  Lys  Ser  Cys  Arg  Leu
            35                      40                  45

Glu  Leu  Ser  Thr  Lys  Asn  Arg  Glu  Arg  Trp  Cys  His  Glu  Ile  Gln  Ile
     50                      55                      60

Met  Lys  Lys  Leu  Asn  His  Ala  Asn  Val  Val  Lys  Ala  Cys  Asp  Val  Pro
65                      70                      75                      80

Glu  Glu  Leu  Asn  Ile  Leu  Ile  His  Asp  Val  Pro  Leu  Leu  Ala  Met  Glu
                    85                      90                      95

Tyr  Cys  Ser  Gly  Gly  Asp  Leu  Arg  Lys  Leu  Leu  Asn  Lys  Pro  Glu  Asn
               100                     105                     110

Cys  Cys  Gly  Leu  Lys  Glu  Ser  Gln  Ile  Leu  Ser  Leu  Leu  Ser  Asp  Ile
              115                     120                     125

Gly  Ser  Gly  Ile  Arg  Tyr  Leu  His  Glu  Asn  Lys  Ile  Ile  His  Arg  Asp
         130                     135                     140

Leu  Lys  Pro  Glu  Asn  Ile  Val  Leu  Gln  Asp  Val  Gly  Gly  Lys  Ile  Ile
145                     150                     155                     160

His  Lys  Ile  Ile  Asp  Leu  Gly  Tyr  Ala  Lys  Asp  Val  Asp  Gln  Gly  Ser
                   165                     170                     175

Leu  Cys  Thr  Ser  Phe  Val  Gly  Thr  Leu  Gln  Tyr  Leu  Ala  Pro  Glu  Leu
              180                     185                     190
```

```
Phe Glu Asn Lys Pro Tyr Thr Ala Thr Val Asp Tyr Trp Ser Phe Gly
            195                 200                 205
Thr Met Val Phe Glu Cys Ile Ala Gly Tyr Arg Pro Phe Leu His His
    210                 215                 220
Leu Gln Pro Phe Thr Trp His Glu Lys Ile Lys Lys Asp Pro Lys
225                 230                 235                 240
Cys Ile Phe Ala Cys Glu Glu Met Ser Gly Glu Val Arg Phe Ser Ser
                245                 250                 255
His Leu Pro Gln Pro Asn Ser Leu Cys Ser Leu Ile Val Glu Pro Met
            260                 265                 270
Glu Asn Trp Leu Gln Leu Met Leu Asn Trp Asp Pro Gln Arg Gly
    275                 280                 285
Gly Pro Val Asp Leu Thr Leu Lys Gln Pro Arg Cys Phe Val Leu Met
    290                 295                 300
Asp His Ile Leu Asn Leu Lys Ile Val His Ile Leu Asn Met Thr Ser
305                 310                 315                 320
Ala Lys Ile Ile Ser Phe Leu Leu Pro Pro Asp Glu Ser Leu His Ser
                325                 330                 335
Leu Gln Ser Arg Ile Glu Arg Glu Thr Gly Ile Asn Thr Gly Ser Gln
            340                 345                 350
Glu Leu Leu Ser Glu Thr Gly Ile Ser Leu Asp Pro Arg Lys Pro Ala
        355                 360                 365
Ser Gln Cys Val Leu Asp Gly Val Arg Gly Cys Asp Ser Tyr Met Val
    370                 375                 380
Tyr Leu Phe Asp Lys Ser Lys Thr Val Tyr Glu Gly Pro Phe Ala Ser
385                 390                 395                 400
Arg Ser Leu Ser Asp Cys Val Asn Tyr Ile Val Gln Asp Ser Lys Ile
                405                 410                 415
Gln Leu Pro Ile Ile Gln Leu Arg Lys Val Trp Ala Glu Ala Val His
            420                 425                 430
Tyr Val Ser Gly Leu Lys Glu Asp Tyr Ser Arg Leu Phe Gln Gly Gln
        435                 440                 445
Arg Ala Ala Met Leu Ser Leu Leu Arg Tyr Asn Ala Asn Leu Thr Lys
    450                 455                 460
Met Lys Asn Thr Leu Ile Ser Ala Ser Gln Gln Leu Lys Ala Lys Leu
465                 470                 475                 480
Glu Phe Phe His Lys Ser Ile Gln Leu Asp Leu Glu Arg Tyr Ser Glu
                485                 490                 495
Gln Met Thr Tyr Gly Ile Ser Ser Glu Lys Met Leu Lys Ala Trp Lys
            500                 505                 510
Glu Met Glu Glu Lys Ala Ile His Tyr Ala Glu Val Gly Val Ile Gly
        515                 520                 525
Tyr Leu Glu Asp Gln Ile Met Ser Leu His Ala Glu Ile Met Glu Leu
    530                 535                 540
Gln Lys Ser Pro Tyr Gly Arg Arg Gln Gly Asp Leu Met Glu Ser Leu
545                 550                 555                 560
Glu Gln Arg Ala Ile Asp Leu Tyr Lys Gln Leu Lys His Arg Pro Ser
                565                 570                 575
Asp His Ser Tyr Ser Asp Ser Thr Glu Met Val Lys Ile Ile Val His
            580                 585                 590
Thr Val Gln Ser Gln Asp Arg Val Leu Lys Glu Leu Phe Gly His Leu
        595                 600                 605
Ser Lys Leu Leu Gly Cys Lys Gln Lys Ile Ile Asp Leu Leu Pro Lys
```

-continued

|  |  |  |  |  | 610 |  |  |  |  | 615 |  |  |  |  | 620 |  |
|---|---|---|---|---|---|---|---|---|---|---|---|---|---|---|---|---|
| Val 625 | Glu | Val | Ala | Leu | Ser 630 | Asn | Ile | Lys | Glu | Ala 635 | Asp | Asn | Thr | Val | Met 640 |
| Phe | Met | Gln | Gly | Lys 645 | Arg | Gln | Lys | Glu | Ile 650 | Trp | His | Leu | Leu | Lys 655 | Ile |
| Ala | Cys | Thr | Gln 660 | Ser | Ser | Ala | Arg | Ser 665 | Leu | Val | Gly | Ser | Ser 670 | Leu | Glu |
| Gly | Ala | Val 675 | Thr | Pro | Gln | Thr | Ser 680 | Ala | Trp | Leu | Pro | Pro 685 | Thr | Ser | Ala |
| Glu | His 690 | Asp | His | Ser | Leu | Ser 695 | Cys | Val | Val | Thr | Pro 700 | Gln | Asp | Gly | Glu |
| Thr 705 | Ser | Ala | Gln | Met | Ile 710 | Glu | Glu | Asn | Leu | Asn 715 | Cys | Leu | Gly | His | Leu 720 |
| Ser | Thr | Ile | Ile | His 725 | Glu | Ala | Asn | Glu | Glu 730 | Gln | Gly | Asn | Ser | Met 735 | Met |
| Asn | Leu | Asp | Trp 740 | Ser | Trp | Leu | Thr | Glu 745 | | | | | | | |

IKK-β PROTEINS, NUCLEIC ACIDS AND METHODS

This a continuing application under 35USC120 of U.S. Ser. No. 08/887,114 filed Jul. 1, 1997, abandoned.

FIELD OF THE INVENTION

The field of this invention is proteins involved in transcription factor activation.

BACKGROUND

Cytokines trigger changes in gene expression by modifying the activity of otherwise latent transcription factors (Hill and Treisman, 1995). Nuclear factor κB (NF-κB) is a prominent example of how such an external stimulus is converted into an active transcription factor (Verma et al., 1995). The NF-κB system is composed of homo- and heterodimers of members of the Rel family of related transcription factors that control the expression of numerous immune and inflammatory response genes as well as important viral genes (Lenardo and Baltimore, 1989; Baeuerle and Henkel, 1994). The activity of NF-κB transcription factors is regulated by their subcellular localization (Verma et al., 1995). In most cell types, NF-κB is present as a heterodimer comprising of a 50 kDa and a 65 kDa subunit. This heterodimer is sequestered in the cytoplasm in association with IκBα a member of the IκB family of inhibitory proteins (Finco and Baldwin, 1995; Thanos and Maniatis, 1995; Verma et al., 1995). IκBα masks the nuclear localization signal of NF-κB and thereby prevents NF-κB nuclear translocation. Conversion of NF-κB into an active transcription factor that translocates into the nucleus and binds to cognate DNA sequences requires the phosphorylation and subsequent ubiquitin-dependent degradation of IκBα in the 26s proteasome. Signal-induced phosphorylation of IκBα occurs at serines 32 and 36. Mutation of one or both of these serines renders IκBα resistant to ubiquitination and proteolytic degradation (Chen et al., 1995).

The pleiotropic cytokines tumor necrosis factor (TNF) and interleukin-1 (IL-1) are among the physiological inducers of IκB phosphorylation and subsequent NF-κB activation (Osborn et al., 1989; Beg et al., 1993). Although TNF and IL-1 initiate signaling cascades leading to NF-κB activation via distinct families of cell-surface receptors (Smith et al., 1994; Dinarello, 1996), both pathways utilize members of the TNF receptor-associated factor (TRAF) family of adaptor proteins as signal transducers (Rothe et al., 1995; Hsu et al., 1996; Cao et al., 1996b). TRAF proteins were originally found to associate directly with the cytoplasmic domains of several members of the TNF receptor family including the 75 kDa TNF receptor (TNFR2), CD40, CD30, and the lymphotoxin-β receptor (Rothe et al., 1994; Hu et al., 1994; Cheng et al., 1995; Mosialos et al., 1995; Song and Donner, 1995; Sato et al., 1995; Lee et al., 1996; Gedrich et al., 1996; Ansieau et al., 1996). In addition, TRAP proteins are recruited indirectly to the 55 kDa TNF receptor (TNFR1) by the adaptor protein TRADD (Hsu et al., 1996). Activation of NF-κB by TNF requires TRAF2 (Rothe et al., 1995; Hsu et al., 1996). TRAF5 has also been implicated in NF-κB activation by members of the TNF receptor family (Nakano et al., 1996). In contrast, TRAF6 participates in NF-κB activation by IL-1 (Cao et al., 1996b). Upon IL-1 treatment, TRAF6 associates with IRAK, a serine-threonine kinase that binds to the IL-1 receptor complex (Cao et al., 1996a).

The NF-κB-inducing kinase (NIK) is a member of the MAP kinase kinase kinase (MAP3K) family that was identified as a TRAF2-interacting protein (Malinin et al., 1997). NIK activates NF-κB when overexpressed, and kinase-inactive mutants of NIK comprising its TRAF2-interacting C-terminal domain ($NIK_{(624-947)}$) or lacking two crucial lysine residues in its kinase domain ($NIK_{KK429-430AA}$) behave as dominant-negative inhibitors that suppress TNF-, IL-1-, and TRAF2-induced NF-κB activation (Malinin et al., 1997). Recently, NIK was found to associate with additional members of the TRAP family, including TRAF5 and TRAF6. Catalytically inactive mutants of NIK also inhibited TRAF5- and TRAF6-induced NF-κB activation, thus providing a unifying concept for NIK as a common mediator in the NF-κB signaling cascades triggered by TNF and IL-1 downstream of TRAFs.

Here, we disclose a novel kinase IκB Kinase, IKK-β, as a NIK-interacting protein. IKK-β has sequence similarity to the conceptual translate of a previously identified open reading frame postulated to encode a serine-threonine kinase of unknown function ('Conserved Helix-loop-helix Ubiquitous Kinase' or CHUK, Connelly and Marcu, 1995; Mock et al., 1995). Catalytically inactive mutants of IKK-β are shown to suppress NF-κB activation induced by TNF and IL-1 stimulation as well as by TRAF and NIK overexpression; transiently expressed IKK-β is shown to associate with the endogenous IκBα complex; and IKK-β is shown to phosphorylate IκBα on serines 32 and 36. As used herein, Ser32 and Ser36 of IκB refers collectively to the two serine residues which are part of the consensus sequence DSGL/IXSM/L (e.g. ser 32 and 36 in IκBα, ser 19 and 23 in IκBβ, and ser 157 and 161, or 18 and 22, depending on the usage of methionines, in IκBε, respectively.

SUMMARY OF THE INVENTION

The invention provides methods and compositions relating to isolated IKK-β polypeptides, related nucleic acids, polypeptide domains thereof having IKK-β-specific structure and activity and modulators of IKK-β function, particularly IκB kinase activity. IKK-β polypeptides can regulate NFκB activation and hence provide important regulators of cell function. The polypeptides may be produced recombinantly from transformed host cells from the subject IKK-β polypeptide encoding nucleic acids or purified from mammalian cells. The invention provides isolated IKK-β hybridization probes and primers capable of specifically hybridizing with the disclosed IKK-β gene, IKK-β-specific binding agents such as specific antibodies, and methods of making and using the subject compositions in diagnosis (e.g. genetic hybridization screens for IKK-β transcripts), therapy (e.g. IKK-β kinase inhibitors to inhibit TNF signal transduction) and in the biopharmaceutical industry (e.g. as immunogens, reagents for isolating other transcriptional regulators, reagents for screening chemical libraries for lead pharmacological agents, etc.).

DETAILED DESCRIPTION OF THE INVENTION

The nucleotide sequence of a natural cDNA encoding a human IKK-β polypeptide is shown as SEQ ID NO: 1, and the full conceptual translate is shown as SEQ ID NO: 2. The IKK-β polypeptides of the invention include incomplete translates of SEQ ID NO: 1 and deletion mutants of SEQ ID NO: 2, which translates and deletion mutants have IKK-β-specific amino acid sequence and binding specificity or function.

The IKK-β polypeptide domains of the invention have amino acid sequences distinguishable from IKK-α, generally at least 11, preferably at least 21, more preferably at least 31 consecutive residues of SEQ ID NO: 2 and provide IKK-β domain specific activity or function, such as IKK-β-specific kinase or kinase inhibitory activity, NIK-binding or binding inhibitory activity, IκB-binding or binding inhibitory activity, NFκB activating or inhibitory activity or antibody binding. Preferred domains phosphorylate at least one and preferably both the serine 32 and 36 of IκB (Verma, I. M., et al. (1995)).

IKK-β-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an IKK-β polypeptide with a binding target is evaluated. The binding target may be a natural intracellular binding target such as an IKK-β substrate, a IKK-β regulating protein or other regulator that directly modulates IKK-β activity or its localization; or non-natural binding target such a specific immune protein such as an antibody, or an IKK-β specific agent such as those identified in screening assays such as described below. IKK-β-binding specificity may assayed by kinase activity or binding equilibrium constants (usually at least about $10^7 M^{-1}$, preferably at least about $10^8 M^{-1}$, more preferably at least about $10^9 M^{-1}$), by the ability of the subject polypeptide to function as negative mutants in IKK-β-expressing cells, to elicit IKK-β specific antibody in a heterologous host (e.g a rodent or rabbit), etc. In any event, the IKK-β binding specificity of the subject IKK-β polypeptides necessarily distinguishes IKK-α (SEQ ID NO: 4).

The claimed IKK-β polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. The IKK-β polypeptides and polypeptide domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides binding agents specific to the subject kinase proteins including substrates, agonists, antagonists, natural intracellular binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper utilization of a pathway involving the subject proteins, e.g. NF-κB activation. Novel IKK-β-specific binding agents include IKK-β-specific receptors, such as somatically recombined polypeptide receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. Agents of particular interest modulate IKK-β function, e.g.

IKK-β-dependent transcriptional activation. For example, a wide variety of inhibitors of IKK-β IκB kinase activity may be used to regulate signal transduction involving IκB. Exemplary IKK-β IκB kinase inhibitors include known classes of serine/threonine kinase (e.g. PKC) inhibitors such as competitive inhibitors of ATP and substrate binding, antibiotics, IKK-β-derived peptide inhibitors, etc., see Tables 1 and 2. IKK-β specificity and activity are readily quantified in high throughput kinase assays using panels of protein kinases (see cited references and Examples).

Preferred inhibitors include natural compounds such as staurosporine (Omura S, et al. J Antibiot (Tokyo) 1995 July;48(7):535–48), produced by a marine organism, and synthetic compounds such as PD 153035, which also potently inhibits the EGF receptor protein kinase (Fry D W et al. Science 1994 Aug. 19;265(5175):1093–5). Members of the tyrphostin family of synthetic protein kinase inhibitors are also useful; these include compounds which are pure ATP competitors, compounds which are pure substrate competitors, and compounds which are mixed competitors: compete with both ATP and substrate (Levitzki A and Gazit A, Science 1995 Mar 24;267(5205):1782–8). Additional IKK-β inhibitors include peptide-based substrate competitors endogenously made by the mammalian cell, e.g. PKI (protein kinase inhibitor, Seasholtz A F et al., Proc Natl Acad Sci USA 1995 Feb. 28;92(5):1734–8), or proteins inhibiting cdc kinases (Correa-Bordes J and Nurse P, Cell 1995 Dec. 15;83(6):1001–9). Additional small peptide based substrate competitive kinase inhibitors and allosteric inhibitors (inhibitory mechanisms independent of ATP or substrate competition) are readily generated by established methods (Hvalby O, et al. Proc Natl Acad Sci USA 1994 May 24;91(11):4761–5; Barja P, et al., Cell Immunol 1994 January;153(1):28–38; Villar-Palasi C, Biochim Biophys Acta 1994 Dec. 30;1224(3):384–8; Liu W Z, et al., Biochemistry 1994 Aug. 23;33(33):10120–6).

TABLE I

Selected Small Molecule IKK-β Kinase Inhibitors

| Inhibitors | Citations |
|---|---|
| HA-100[1] | 1. Hagiwara, M,. et al. Mol. Pharmacol. 32:7 (1987) |
| Chelerythrine[2] | 2. Herbert, J. M., et al. Biochem Biophys Res Com 172:993 (1990) |
| Staurosporine[3,4,5] | 3. Schachtele, C., et al. Biochem Biophys Res Com 151:542 (1988) |
| Calphostin C[6,7,8,9] | 4. Tamaoki, T., et al. Biochem Biophys Res Com 135:397 (1986) |
| K-252b[10] | 5. Tischler, A. S., et al. J. Neurochemistry 55:1159 (1990) |
| PKC 19-36[11] | 6. Bruns, R. F., et al. Biochem Biophys Res Com 176:288 (1991) |
| Iso-H7[12] | 7. Kobayashi, E., et al. Biochem Biophys Res Com 159:548 (1989) |
| PKC 19-31 | 8. Tamaoki, T., et al Adv 2nd Mass Phosphoprotein Res 24:497 (1990) |
| H-7[13,3,14] | 9. Tamaoki, T., et al. Biotechnology 8:732 (1990) |
| H-89[15] | 10. Yasuzawa, T. J. Antibiotics 39:1972 (1986) |
| KT5720[16] | 11. House, C., et al. Science 238:1726 (1987) |
| cAMP-depPKinhib[17] | 12. Quick, J., et al. Biochem. Biophys. Res. Com. 167:657 (1992) |
| A-3[18] | 13. Bouli, N. M. and Davis, M. Brain Res. 525:198 (1990) |
| HA1004[19,20] | 14. Takahashi, I., et al. J. Pharmacol. Exp. Ther. 255:1218 (1990) |

TABLE I-continued

Selected Small Molecule IKK-β Kinase Inhibitors

| Inhibitors | Citations |
|---|---|
| K-252a[16,5] | 15. Chijiwa, T., et al. J. Biol. Chem. 265:5267 (1990) |
| KT5823[16] | 16. Kase, H., et al. Biochem. Biophys. Res. Com. 142:436 (1987) |
| ML-9[21] | 17. Cheng, H. C., et al. J. Biol. Chem. 261:989 (1986) |
| KT5926[22] | 18. Inagaki, M., et al. Mol. Pharmacol. 29:577 (1986) |
| | 19. Asano, T. and Hidaka, H. J Pharmaco. Exp Ther 231:141 (1984) |
| | 20. Hidaka, H., et al. Biochemistry 23:5036 (1984) |
| | 21. Nagatsu, T., et al. Biochem Biophys Res Com 143:1045 (1987) |
| | 22. Nakanishi, S., et al. Mol. Pharmacol. 37:482 (1990) |

TABLE II

Selected Peptidyl IKK-β Kinase Inhibitors

| | |
|---|---|
| hIκBα, residues 24–39, 32Ala | hIKK-β, Δ5–203 |
| hIκBα, residues 29–47, 36Ala | hIKK-β, Δ1–178 |
| hIκBα, residues 26–46, 32/36Ala | hIKK-β, Δ368–756 |
| hIκBβ, residues 25–38, 32Ala | hIKK-β, Δ460–748 |
| hIκBβ, residues 30–41, 36Ala | hIKK-α, Δ1–289 |
| hIκBβ, residues 26–46, 32/36Ala | hIKK-α, Δ12–219 |
| hIκBε, residues 24–40, 32Ala | hIKK-α, Δ307–745 |
| hIκBε, residues 31–50, 36Ala | hIKK-α, Δ319–644 |
| hIκBε, residues 27–44, 32/36Ala | |

Accordingly, the invention provides methods for modulating signal transduction involving IκB in a cell comprising the step of modulating IKK-β kinase activity, e.g. by contacting the cell with a serine/threonine kinase inhibitor. The cell may reside in culture or in situ, i.e. within the natural host. Preferred inhibitors are orally active in mammalian hosts. For diagnostic uses, the inhibitors or other IKK-β binding agents are frequently labeled, such as with fluorescent, radioactive, chemiluminescent, or other easily detectable molecules, either conjugated directly to the binding agent or conjugated to a probe specific for the binding agent.

The amino acid sequences of the disclosed IKK-β polypeptides are used to back-translate IKK-β polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural IKK-β-encoding nucleic acid sequences ("GCG" software, Genetics Computer Group, Inc, Madison Wis.). IKK-β-encoding nucleic acids used in IKK-β-expression vectors and incorporated into recombinant host cells, e.g. for expression and screening, transgenic animals, e.g. for functional studies such as the efficacy of candidate drugs for disease associated with IKK-β-modulated cell function, etc.

The invention also provides nucleic acid hybridization probes and replication/amplification primers having a IKK-β cDNA specific sequence contained in SEQ ID NO: 1 and sufficient to effect specific hybridization thereto (i.e. specifically hybridize with SEQ ID NO: 1 in the presence of IKK-α cDNA, SEQ ID NO: 3). Such primers or probes are at least 12, preferably at least 24, more preferably at least 36 and most preferably at least 96 bases in length. Demonstrating specific hybridization generally requires stringent conditions, for example, hybridizing in a buffer comprising 30% formamide in 5×SSPE (0.18M NaCl, 0.01M NaPO$_4$, pH7.7, 0.001M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. IKK-β nucleic acids can also be distinguished using alignment algorithms, such as BLASTX (Altschul et al. (1990) Basic Local Alignment Search Tool, J Mol Biol 215, 403–410).

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant nucleic acids comprising the nucleotide sequence of SEQ ID NO: 1 or fragments thereof, contain such sequence or fragment at a terminus, immediately flanked by a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of IKK-β genes and gene transcripts and in detecting or amplifying nucleic acids encoding additional IKK-β homologs and structural analogs. In diagnosis, IKK-β hybridization probes find use in identifying wild-type and mutant IKK-β alleles in clinical and laboratory samples. Mutant alleles are used to generate allele-specific oligonucleotide (ASO) probes for high-throughput clinical diagnoses. In therapy, therapeutic IKK-β nucleic acids are used to modulate cellular expression or intracellular concentration or availability of active IKK-β.

The invention provides efficient methods of identifying agents, compounds or lead compounds for agents active at the level of a IKK-β modulatable cellular function. Generally, these screening methods involve assaying for compounds which modulate IKK-β interaction with a natural IKK-β binding target, in particular, IKK-β phosphorylation of IκB-derived substrates, particularly IκB and NIK substrates. A wide variety of assays for binding agents are provided including labeled in vitro protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including an IKK-β polypeptide, which may be part of a fusion product with another peptide or polypeptide, e.g. a tag for detection or anchoring, etc. The assay mixtures comprise a natural intracellular IKK-β binding target. In a particular embodiment, the binding target is a substrate comprising IκB serines 32 and/or 36. Such substrates comprise a IκBα, β or ε peptide including the serine 32 and/or 36 residue and at least 5, preferably at least 10, and more preferably at least 20 naturally occurring immediately flanking residues on each side (e.g. for serine 36 peptides, residues 26–46, 22–42, or 12–32 or 151–171 for IκBα, β or ε -derived substrates, respectively). While native full-length binding targets may be used, it is frequently preferred to use portions (e.g. peptides) thereof so long as the portion provides binding affinity and avidity to the subject IKK-β polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like ATP or ATP analogs (for kinase assays), salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the IKK-β polypeptide specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the IKK-β polypeptide and one or more binding targets is detected by any convenient way. For IKK-β kinase assays, 'binding' is generally detected by a change in the phosphorylation of a IKK-β substrate. In this embodiment, kinase activity may quantified by the transfer to the substrate of a labeled phosphate, where the label may provide for direct detection as radioactivity, luminescence, optical or electron density, etc. or indirect detection such as an epitope tag, etc. A variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the IKK-β polypeptide to the target in the absence of the agent as compared with the binding affinity in the presence of the agent indicates that the agent modulates the binding of the IKK-β polypeptide to the IKK-β binding target. Analogously, in the cell-based assay also described below, a difference in IKK-β-dependent transcriptional activation in the presence and absence of an agent indicates the agent modulates IKK-β function. A difference, as used herein, is statistically significant and preferably represents at least a 50%, more preferably at least a 90% difference.

The following experimental section and examples are offered by way of illustration and not by way of limitation.

EXPERIMENTAL

Identification of IKK-β

To investigate the mechanism of NIK-mediated NF-κB activation, we initially identified proteins that associate directly with NIK by yeast two-hybrid protein interaction cloning (Fields and Song, 1989). An expression vector was generated that encodes NIK fused to the DNA-binding domain of the yeast transcription factor GAL4. This vector was used as bait in a two-hybrid screen of a human B cell cDNA library. From approximately six million transformants, eight positive clones were obtained, as determined by activation of his and lacZ reporter genes. Of these clones, three encoded a member of the TRAF family, TRAF3 (Hu et al., 1994; Cheng et al., 1995; Mosialos et al., 1995; Sato et al., 1995) and one encoded a novel protein we call IKK-α. Retransformation into yeast cells verified the interaction between NIK and IKK-α. A full-length human IKK-α clone was isolated by screening a Jurkat cDNA library with a probe generated from the 5'-end of the IKK-α two-hybrid clone. IKK-α comprises an N-terminal serine-threonine kinase catalytic domain, a C-terminal helix-loop-helix domain and a leucine zipper-like amphipathic α-helix juxtaposed in between the helix-loop-helix and kinase domain.

To identify potential IKK-α-related genes, we searched a public database of human expressed sequence tags (ESTs). We identified two ESTs (W68756 and AA128064), which we determined were capable of encoding distinct peptides with sequence similarity with IKK-α. IKK-α-related cDNA was cloned by probing a Jurkat cDNA library (human T cell) with an oligonucleotide probe corresponding to sequence from one of the ESTs. Sequence analysis demonstrated that the two ESTs included different fragments of the same gene. The longest cDNA clones obtained had a ~3.2 kb insert (SEQ ID NO: 1) and an open reading frame of 756 amino acids (SEQ ID NO: 2). We have designed the protein encoded by this cDNA as IKK-β.

Interaction of IKK-β and NIK in Human Cells

The interaction of IKK-β with NIK was confirmed in mammalian cell coimmunoprecipitation assays. Human IKK-β containing an C-terminal Flag epitope tag was transiently coexpressed in 293 human embryonic kidney cells with Myc epitope-tagged NIK. Cell lysates were immunoprecipitated using a monoclonal antibody against the Flag epitope, and coprecipitating NIK was detected by immunoblot analysis with an anti-Myc monoclonal antibody. In this assay, IKK-β was able to coprecipitate NIK confirming the interaction between both proteins as detected for IKK-α by yeast two-hybrid analysis. Also, a deletion mutant IKK-β protein lacking most of the N-terminal kinase domain (IKK-$\beta_{(\Delta 5\text{-}203, \text{ i.e. } 1\text{-}4 \text{ \& } 204\text{-}756)}$) was able to associate with NIK, indicating that the α-helical C-terminal half of IKK-β mediates the interaction with NIK.

Effect of IKK-β and IKK-β Mutants on NF-κB Activation

To investigate a possible role for IKK-β in NF-κB activation, we examined if transient overexpression of IKK-β might activate an NF-κB-dependent reporter gene. An E-selectin-luciferase reporter construct (Schindler and Baichwal, 1994) and a IKK-β expression vector were cotransfected into HeLa cells. IKK-β expression activated the reporter gene in a dose-dependent manner, with a maximal induction of luciferase activity of about 20-fold compared to vector control. Similar results were obtained in 293 cells, where IKK-β overexpression induced reporter gene activity approximately 20-fold. Thus, IKK-β induces NF-κB activation when overexpressed.

We next determined the effect of overexpression of kinase-inactive IKK-$\beta_{(\Delta 5\text{-}203)}$ that still associates with NIK on signal-induced NF-κB activation in reporter gene assays in 293 cells. Overexpression of IKK-$\beta_{(\Delta 5\text{-}203)}$ blocked TNF- and IL-1-induced reporter gene activation similar to overexpression of NIK$_{(624\text{-}947)}$. IKK-$\beta_{(\Delta 5\text{-}203)}$ was also found to inhibited NF-κB-dependent reporter gene activity elicited by overexpression of TRAF2, TRAF6 and NIK. Taken together these results demonstrate that a catalytically inactive IKK-β mutant is a dominant-negative inhibitor of TNF-, IL-1, TRAF- and NIK-induced NF-κB activation. This indicates that IKK-β functions as a common mediator of NF-κB activation by TNF and IL-1 downstream of NIK.

Parenthetical References

Ansieau, S., et al. (1996). Proc. Natl. Acad. Sci. USA 93, 14053–14058.
Baeuerle, P. A., and Henkel, T. (1994). Annu. Rev. Immunol. 12, 141–179.
Beg, A. A., et al. (1993). Mol. Cell. Biol. 13, 3301–3310.
Cao, Z., Henzel, W. J., and Gao, X. (1996a). Science 271, 1128–1131.
Cao, Z., et al. (1996b).. Nature 383, 443–446.
Chen, Z., et al.. (1995). Genes Dev. 9, 1586–1597.
Cheng, G., et al. (1995). Science 267, 1494–1498.
Connelly, M. A., and Marcu, K. B. (1995). Cell. Mol. Biol. Res. 41, 537–549.
Dinarello, C. A. (1996). Biologic basis for interleukin-1 in disease. Blood 87, 2095–2147.
Fields, S., and Song, O.-k. (1989). Nature 340, 245–246.
Finco, T. S., and Baldwin, A. S. (1995). Immunity 3, 263–272.
Gedrich, R. W., et al. (1996). J. Biol. Chem. 271, 12852–12858.
Hill, C. S., and Treisman, R. (1995). Cell 80, 199–211.
Hsu, H., Shu, H.-B., Pan, M.-P., and Goeddel, D. V. (1996). Cell 84, 299–308.
Hu, H. M., et al. (1994). J. Biol. Chem. 269, 30069–30072.
Lee, S. Y., et al. (1996). Proc. Natl. Acad. Sci. USA 93, 9699–9703.
Lenardo, M., and Baltimore, D. (1989). Cell 58, 227–229.
Malinin, N. L., et al. (1997). Nature 385, 540–544.
Mock et al. (1995). Genomics 27, 348–351.
Mosialos, G., et al. (1995). Cell 80, 389–399.
Nakano, H., et al. (1996). J. Biol. Chem. 271, 14661–14664.
Osborn, L., Kunkel, S., and Nabel, G. J. (1989). Proc. Natl. Acad. Sci. USA 86, 2336–2340.
Rothe, M., Sarma, V., Dixit, V. M., and Goeddel, D. V. (1995). Science 269, 1424–1427.
Rothe, M., Wong, S. C., Henzel, W. J., and Goeddel, D. V. (1994). Cell 78, 681–692.
Sato, T., Irie, S., and Reed, J. C. (1995). FEBS Lett. 358, 113–118.
Schindler, U., and Baichwal, V. R. (1994). Mol. Cell. Biol. 14, 5820–5831.
Smith, C. A., Farrah, T., and Goodwin, R. G. (1994). Cell 76, 959–962.
Song, H. Y., and Donner, D. B. (1995). Biochem. J. 809, 825–829.
Thanos, D., and Maniatis, T. (1995). Cell 80, 529–532.
Verma, I. M., et al. (1995). Genes Dev. 9, 2723–2735.

EXAMPLES

1. Protocol for at IKK-β-IκBα phosphorylation assay.

A. Reagents:
Neutralite Avidin: 20 μg/ml in PBS.
kinase: $10^{-8}$–$10^{-5}$M IKK-β (SEQ ID NO: 2) at 20 μg/ml in PBS.
substrate: $10^{-7}$–$10^{-4}$M biotinylated substrate (21 residue peptide consisting of residues 26–46 of human IκBα) at 40 μg/ml in PBS.
Blocking buffer: 5% BSA, 0.5% Tween 20 in PBS; 1 hour at room temperature.
Assay Buffer: 100 mM KCl, 10 mM $MgCl_2$, 1 mM $MnCl_2$, 20 mM HEPES pH 7.4, 0.25 mM EDTA, 1% glycerol, 0.5% NP-40, 50 mM BME, 1 mg/ml BSA, cocktail of protease inhibitors.

$[^{32}P]\gamma$-ATP 10x stock: $2\times10^{-5}$M cold ATP with 100 μCi $[^{32}P]\gamma$-ATP. Place in the 4° C. microfridge during screening.

Protease inhibitor cocktail (1000x): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM $NaVo_3$ (Sigma # S-6508) in 10 ml of PBS.

B. Preparation of assay plates:
Coat with 120 μl of stock N Avidin per well overnight at 4° C.
Wash 2 times with 200 μl PBS.
Block with 150 μl of blocking buffer.
Wash 2 times with 200 μl PBS.

C. Assay:
Add 40 μl assay buffer/well.
Add 40 μl biotinylated substrate (2–200 pmoles/40 ul in assay buffer)
Add 40 μl kinase (0.1–10 pmoles/40 ul in assay buffer)
Add 10 μl compound or extract
Add 10 μl $[^{32}P]\gamma$-ATP 10x stock.
Shake at 25° C. for 15 minutes.
Incubate additional 45 minutes at 25° C.
Stop the reaction by washing 4 times with 200 μl PBS.
Add 150 μl scintillation cocktail.
Count in Topcount.

D. Controls for all assays (located on each plate):
a. Non-specific binding
b. cold ATP at 80% inhibition.

2. Protocol for high throughput IKK-β-NIK binding assay.

A. Reagents:
Neutralite Avidin: 20 μg/ml in PBS.
Blocking buffer: 5% BSA, 0.5% Tween 20 in PBS; 1 hour at room temperature.
Assay Buffer: 100 mM KCl, 20 mM HEPES pH 7.6, 1 mM $MgCl_2$, 1% glycerol, 0.5% NP-40, 50 mM β-mercaptoethanol, 1 mg/ml BSA, cocktail of protease inhibitors.
$^{33}$P IKK-β polypeptide 10x stock: $10^{-8}$–$10^{-6}$M "cold" IKK-β supplemented with 200,000–250,000 cpm of labeled IKK-β (Beckman counter). Place in the 4° C. microfridge during screening.

Protease inhibitor cocktail (1000X): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM $NaVO_3$ (Sigma # S-6508) in 10 ml of PBS.

NIK: $10^{-7}$–$10^{-5}$M biotinylated NIK in PBS.

B. Preparation of assay plates:
Coat with 120 μl of stock N-Avidin per well overnight at 4° C.
Wash 2 times with 200 μl PBS.
Block with 150 μl of blocking buffer.
Wash 2 times with 200 μl PBS.

C. Assay:
Add 40 μl assay buffer/well.
Add 10 μl compound or extract.
Add 10 μl $^{33}$P-IKK-β (20–25,000 cpm/0.1–10 pmoles/well=$10^{-9}$–$10^{-7}$M final conc).
Shake at 25° C. for 15 minutes.
Incubate additional 45 minutes at 25° C.
Add 40 μM biotinylated NIK (0.1–10 pmoles/40 ul in assay buffer)
Incubate 1 hour at room temperature.
Stop the reaction by washing 4 times with 200 μM PBS.
Add 150 μM scintillation cocktail.
Count in Topcount.

D. Controls for all assays (located on each plate):
  a. Non-specific binding
  b. Soluble (non-biotinylated NIK) at 80% inhibition.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated or recombinant nucleic acid comprising at least 96 consecutive nucleotides of SEQ ID NO: 1.

2. A cell comprising the nucleic acid according to claim 1.

3. An isolated or recombinant nucleic acid according to claim 1, comprising the sequence set forth as SEQ ID NO: 1.

4. A cell comprising the nucleic acid according to claim 3.

5. An isolated or recombinant nucleic acid encoding a polypeptide comprising at least 31 consecutive residues of the amino acid sequence set forth as SEQ ID NO: 2.

6. A cell comprising the nucleic acid according to claim 5.

7. A method of making an isolated polypeptide, said method comprising the steps of:
   introducing the recombinant nucleic acid of claim 5 into a host cell or cellular extract,
   incubating said host cell or cellular extract under conditions whereby said polypeptide is expressed; and
   isolating said polypeptide.

8. An isolated or recombinant nucleic acid according to claim 5 encoding a polypeptide comprising the amino acid sequence set forth as SEQ ID NO: 2.

9. A cell comprising the nucleic acid according to claim 8.

10. A method of making an isolated polypeptide, said method comprising the steps of:
    introducing the recombinant nucleic acid of claim 8 into a host cell or cellular extract,
    incubating said host cell or cellular extract under conditions whereby said polypeptide is expressed; and
    isolating said polypeptide.

11. A method of making an isolated polypeptide, said method comprising the steps of:
    introducing the recombinant nucleic acid encoding a polypeptide comprising at least 11 consecutive residues of the amino acid sequence set forth as SEQ ID NO: 2 into a host cell or cellular extract,
    incubating said host cell or cellular extract under conditions whereby said polypeptide is expressed; and
    isolating said polypeptide.

12. A method of making an isolated polypeptide according to claim 11, said method comprising the steps of:
    introducing the recombinant nucleic acid encoding a polypeptide comprising at least 21 consecutive residues of the amino acid sequence set forth as SEQ ID NO: 2 into a host cell or cellular extract,
    incubating said host cell or cellular extract under conditions whereby said polypeptide is expressed; and
    isolating said polypeptide.

* * * * *